United States Patent
Bonnal

(10) Patent No.: US 10,625,071 B2
(45) Date of Patent: Apr. 21, 2020

(54) CLOSURE DEVICE FOR A FLUID SYSTEM FOR MEDICAL PURPOSES

(71) Applicant: B. Braun Melsungen AG, Melsungen (DE)

(72) Inventor: Oliver Bonnal, Melsungen (DE)

(73) Assignee: B. Braun Melsungen AG (DE)

( * ) Notice: Subject to any disclaimer, the term of this patent is extended or adjusted under 35 U.S.C. 154(b) by 0 days.

(21) Appl. No.: 14/801,894

(22) Filed: Jul. 17, 2015

(65) Prior Publication Data

US 2016/0015960 A1 Jan. 21, 2016

(30) Foreign Application Priority Data

Jul. 17, 2014 (DE) .................. 10 2014 213 947

(51) Int. Cl.
*A61M 39/24* (2006.01)
*A61M 39/10* (2006.01)
*A61M 39/26* (2006.01)

(52) U.S. Cl.
CPC ............ *A61M 39/24* (2013.01); *A61M 39/10* (2013.01); *A61M 39/26* (2013.01); *A61M 2039/1027* (2013.01)

(58) Field of Classification Search
CPC .................. A61M 39/26; A61M 39/24; A61M 2039/2406; A61M 2039/242; A61M 2039/2426; A61M 2039/2433; A61M 2039/2446; A61M 2039/2453; A61M 2039/246; A61M 2039/2466;
(Continued)

(56) References Cited

U.S. PATENT DOCUMENTS 5,843,044 A * 12/1998 Moorehead ........... A61M 16/20
604/247
5,957,898 A * 9/1999 Jepson ................ A61M 39/045
128/912

(Continued)

FOREIGN PATENT DOCUMENTS

EP 0 956 088 B1 7/2010
EP 2 253 351 A1 11/2010

OTHER PUBLICATIONS

"Swept". Merriam-Webster Online Dictionary. <https://www.merriam-webster.com/dictionary/swept> Accessed Dec. 17, 2018.*

*Primary Examiner* — Kami A Bosworth
(74) *Attorney, Agent, or Firm* — RatnerPrestia

(57) ABSTRACT

A closure device for a fluid system for medical purposes is disclosed. The closure device includes a support housing, which has at least one opening to a fluid reservoir or a fluid line, and also with a connection piece, which includes a Luer connecting portion for connecting to a syringe or some other Luer connection part, and with an elastically deformable closure membrane, which closes a fluid passage of the connection piece and opens it when the syringe or other Luer connection part is connected. A nonreturn valve is configured for opening both in the direction of the connection piece and in the direction of the opening to the fluid reservoir or to the fluid line is arranged in the support housing at a distance from the closure membrane in the direction of the fluid. The closure device has applications in several areas, including in infusion systems for medical purposes.

11 Claims, 4 Drawing Sheets

(58) Field of Classification Search
CPC ...... A61M 2039/261; A61M 2039/262; A61M 2039/263; A61M 2039/1027; A61M 39/10; A61M 2039/1083
See application file for complete search history.

(56) References Cited

U.S. PATENT DOCUMENTS

| | | | |
|---|---|---|---|
| 8,454,579 B2 * | 6/2013 | Fangrow, Jr. ......... | A61M 39/24 604/539 |
| 8,662,104 B2 | 3/2014 | Hansmann et al. | |
| 2009/0259175 A1 * | 10/2009 | Nordgren .............. | A61M 39/24 604/30 |
| 2010/0269829 A1 | 10/2010 | Hansmann et al. | |

* cited by examiner

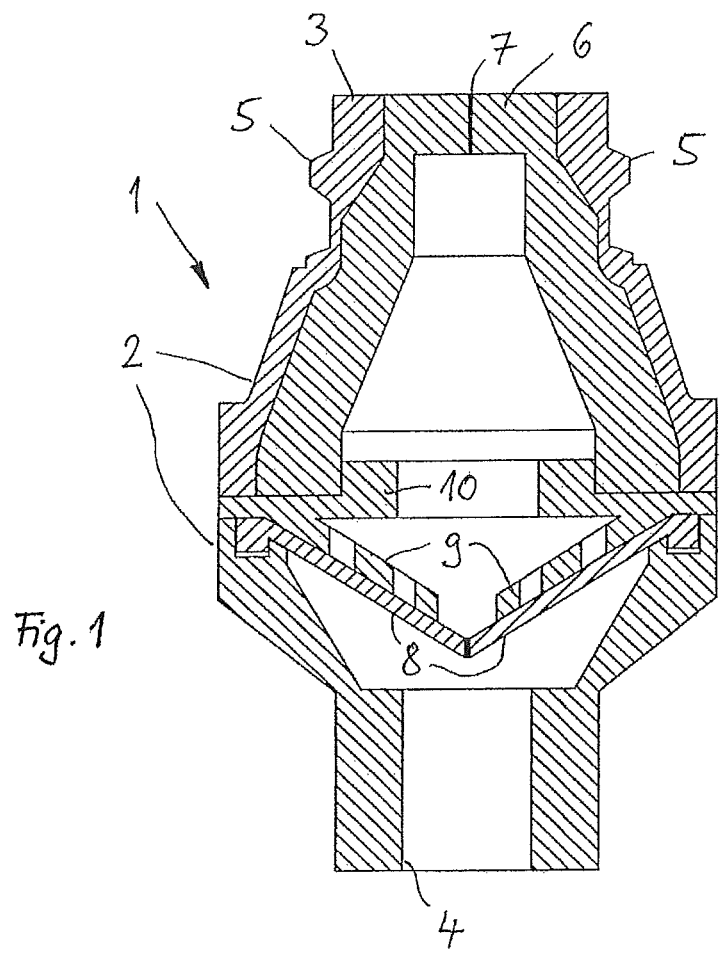

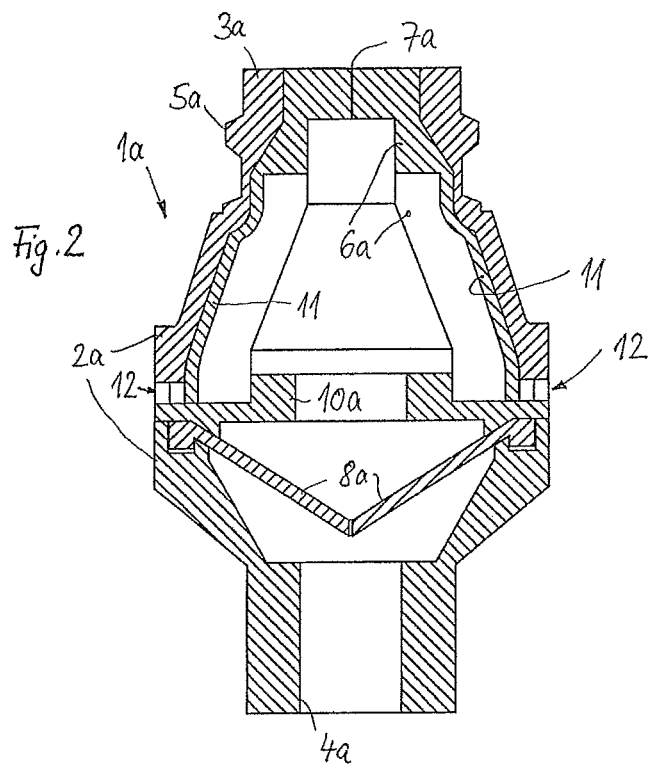
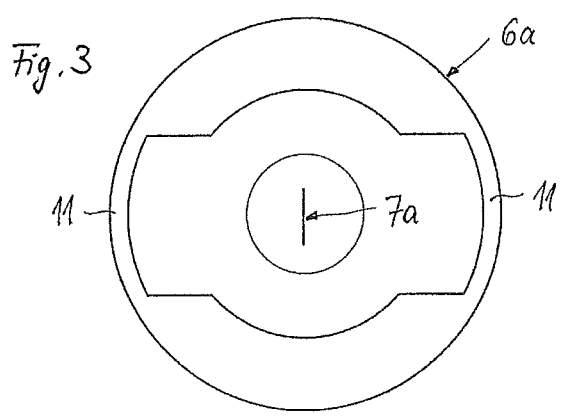

CLOSURE DEVICE FOR A FLUID SYSTEM FOR MEDICAL PURPOSES

CROSS-REFERENCE TO RELATED APPLICATIONS

This application claims priority from German Patent Application No. 10 2014 213 947.3, filed Jul. 17, 2014, the disclosure of which is hereby incorporated by reference in its entirety into this application.

FIELD OF THE DISCLOSED SUBJECT MATTER

The disclosed subject matter relates to a closure device for a fluid system for medical purposes, with a support housing, which has at least one opening to a fluid reservoir or a fluid line, and also with a connection piece, which comprises a Luer connecting portion for connecting to a syringe or some other Luer connection part, and with an elastically deformable closure membrane, which closes a fluid passage of the connection piece and opens it when the syringe or other Luer connection part is connected.

BACKGROUND

Such a closure device is known from EP 0 956 088 B1. The known closure device is configured as a medical valve for controlling the flow of fluid between a medical instrument and a catheter tip of a catheter. The valve has a support housing with a connection piece, the fluid passage of which can be closed by means of an elastically deformable closure membrane. On the basis of FIGS. 28 and 29, a dual valve is also presented in EP 0 956 088 B1, two elastically deformable closure membranes being arranged in series one behind the other in the support housing. The first closure membrane, closing the fluid passage, is opened by the insertion of a syringe or some other Luer connection part. The second closure membrane, at a distance in the direction of the fluid, is opened by corresponding liquid pressure, which occurs by introducing a fluid from the syringe or the Luer connection part into the support housing of the closure device.

SUMMARY

The problem addressed by the disclosed subject matter is that of providing a closure device of the type mentioned at the beginning that makes it possible for a fluid to be both delivered and extracted.

This problem is solved by arranging a nonreturn valve that is capable of opening both in the direction of the connection piece and in the direction of the opening to the fluid reservoir or to the fluid line in the support housing at a distance from the closure membrane in the direction of the fluid. The nonreturn valve connected downstream of the closure membrane within the support housing can consequently open in both directions of the fluid, and so, with a syringe connected to the connecting portion of the connection piece, or some other Luer connection part that is connected to the connection piece, fluid can be both delivered and extracted. Depending on the configuration of the fluid system, apart from delivering a medical fluid, it is also possible to extract blood from a patient or a medical fluid from a fluid system by way of the connection piece. The solution according to the disclosed subject matter is suitable in a particularly advantageous way for medical infusion or transfusion systems and is used in particular in the case of inpatient treatment. It makes handling easy for carers or nursing staff, since fluid can flow in both directions by way of the connection piece of the closure device, and so enables carers or nursing staff both to deliver fluid and to extract fluid easily by way of the same closure device. In this way, unintentional contact of carers or nursing staff with corresponding fluid during the handling of the closure device, the syringe or other Luer connection part can be avoided. Moreover, a return flow of blood from the support housing can be avoided. The closure device according to the disclosed subject matter also ensures that no impurities that could harm the patient can occur in the fluid as a result of contamination with ambient air.

In a refinement of the disclosed subject matter, the nonreturn valve is designed in such a way that it opens in the direction of the opening to the fluid reservoir or the fluid line at a smaller difference in pressure than in the opposite direction to the fluid passage of the connection piece. This ensures that, when the syringe or other Luer connection part is detached from the connection piece, there is no unintentional escape of fluid located in the support housing as a result of negative pressure occurring for a short time.

In a further refinement of the disclosed subject matter, the difference in pressure at which the nonreturn valve opens towards the opening is at least three times smaller, preferably five times smaller, than in the opposite direction to the fluid passage of the connection piece. This ensures that the nonreturn valve only opens for extraction of fluid in the direction of the fluid passage of the connection piece when a sufficiently high pressure has been created by the filling of a syringe. On the other hand, the difference in pressure that is briefly created by detachment of the syringe or other Luer connection part from the connection piece is not sufficient to open the nonreturn valve in the direction of the fluid passage of the connection piece.

In a further refinement of the disclosed subject matter, the difference in pressure at which the nonreturn valve opens towards the fluid passage of the connection piece is greater than a difference in pressure that is created when the syringe or other Luer connection part is detached from the connection piece of the support housing. In this way, an unintentional outflow or return flow of fluid when the syringe or other Luer connection part is detached is reliably avoided, since the nonreturn valve remains closed for these handling cases.

In a further refinement of the disclosed subject matter, mechanical supporting means assigned to the nonreturn valve on one side are provided in the support housing, in order only to bring about the opening of the nonreturn valve in the one direction of the fluid at a greater difference in pressure than in the opposite direction of the fluid. The mechanical effect of supporting the nonreturn valve makes it possible for the nonreturn valve to open in opposite directions at different differences in pressure. The mechanical supporting means may be formed in the support housing and flank the nonreturn valve in parallel on one side. Alternatively, the supporting means may also be integrated in the material of the nonreturn valve, preferably in the form of reinforcing ribs or in the form of a two-component production of the nonreturn valve, the supporting means representing the plastic component that is dimensionally more stable than an elastomer component of the nonreturn valve.

In a further refinement of the disclosed subject matter, the nonreturn valve is assigned on the side facing the fluid passage in the support housing a variable pressure-equalizing chamber, which equalizes differences in pressure that lead to undesired premature opening of the nonreturn valve. The pressure-equalizing chamber is provided instead of mechanical supporting means to allow the nonreturn valve to open in opposite directions when there are different differences in pressure.

In a further refinement of the disclosed subject matter, the variable pressure-equalizing chamber comprises elastically flexible wall portions, which curve outwardly or inwardly depending on the fluid pressure, and thus change the volume of the pressure-equalizing chamber. The elastically flexible wall portions may preferably be formed by a fanfold-like annular wall, which is arranged in the support housing. Alternatively, the elastically flexible wall portions may also be integrated in the closure membrane. In the case of this refinement, at least one pressure-equalizing opening to the surroundings, which is arranged in the region of the elastically flexible wall portions of the closure membrane, is also provided in the support housing. If the elastically flexible wall portions of the pressure-equalizing chamber are integrated in the closure membrane, these wall portions are significantly thinner than the other wall portions of the closure membrane, in order to allow elastic deformation of these wall portions and pressure equalization at the desired differences in pressure.

In a further refinement of the disclosed subject matter, between the closure membrane and at least one wall portion of the pressure-equalizing chamber, a mechanical adjusting means, which, depending on closing or opening of the closure member, performs a displacement of the wall portion to bring about a change in volume of the pressure-equalizing chamber, is provided in the support housing. By this mechanical adjusting means it is possible for a detachment or connection of a syringe or some other Luer connection part in relation to the connection piece to be transferred directly to the pressure-equalizing chamber.

In a further refinement of the disclosed subject matter, the support housing is of a one-part or multi-part configuration. In the case of a multi-part configuration, the parts of the support housing may—depending on the configuration—be connected to one another in a non-positively engaging, material-bonding or positively engaging manner.

In a further refinement of the disclosed subject matter, the pressure-equalizing chamber is arranged in a sealed fluid-carrying manner between the closure membrane and the nonreturn valve. As a result, the desired pressure equalization of a corresponding fluid flow for extracting or delivering fluid in relation to the support housing is ensured.

In a further refinement of the disclosed subject matter, the nonreturn valve is designed or supported by the supporting means in such a way that it opens in the direction of the fluid to the fluid passage of the connection piece at a difference in pressure of more than 10 hPa and in the opposite direction of the fluid towards the opening to the fluid reservoir or the fluid line at a difference in pressure of more than 2 hPa. These pressure ranges have proven to be advantageous for easy and functionally reliable handling of the closure device by medical carers or nursing staff.

Further advantages and features of the disclosed subject matter are provided by the claims and the following description of preferred exemplary embodiments of the disclosed subject matter, which are represented on the basis of the drawings.

BRIEF DESCRIPTION OF THE DRAWINGS

FIG. 1 schematically shows a first embodiment of a closure device according to the disclosed subject matter in a sectional representation, FIG. 2 shows a further embodiment of a closure device according to the disclosed subject matter in a sectional representation, FIG. 3 shows a view from below of a closure membrane of the closure device that is shown in FIG. 2.

DETAILED DESCRIPTION

Figure 4:
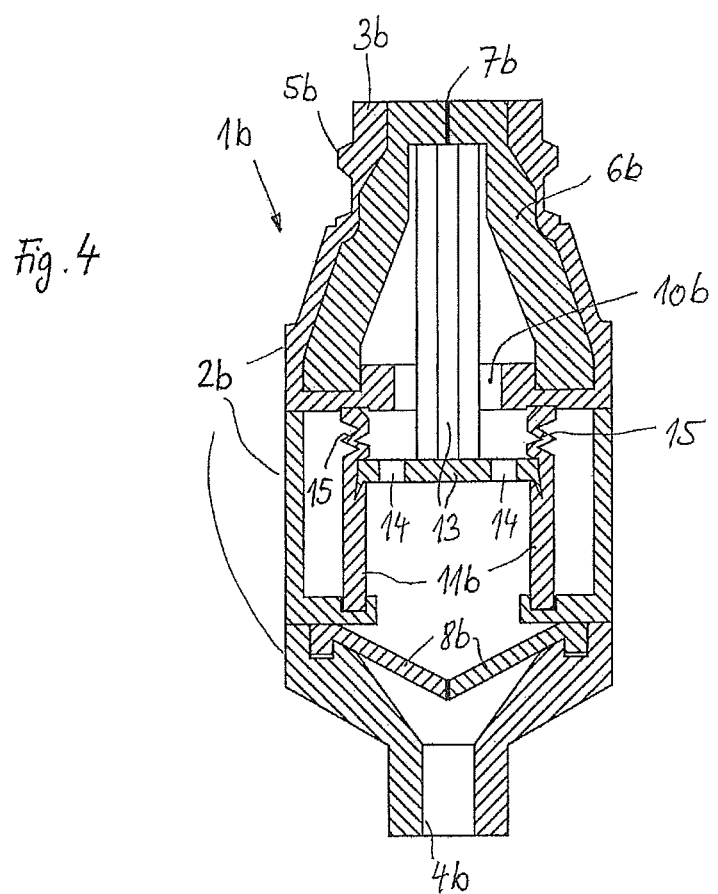
FIG. 4 shows a further embodiment of a closure device according to the disclosed subject matter in a first functional position in a schematic sectional representation and FIG. 5 shows the closure device that is shown in FIG. 4 in a further functional position.

A closure device 1 that is shown FIG. 1 is part of a fluid system for medical purposes, in particular for a medical infusion or transfusion system. The closure device 1 has a support housing 2, which has an opening 4 to a fluid reservoir (not represented) or to a fluid line (not represented), preferably to a catheter of a patient. The fluid reservoir serves for receiving a medical fluid, in particular a medical carrier solution, an infusion solution or else a quantity of blood.

The closure device 1 has a support housing 2, which on one side has a connection piece 3 for connection to a syringe or some other Luer connection part. On the opposite side, the support housing 2 is provided with an opening 4, which leads to the fluid reservoir (not represented) or the fluid line (not represented). The support housing 1 is part of a closed fluid system. The opening 4 also goes over in a sealed manner into the corresponding fluid reservoir or into the corresponding fluid line in a way that is not shown.

The connection piece 3 is provided at its outer circumference with a Luer connecting portion 5. The connection piece 3 also has a fluid passage, which is closed by an elastically deformable closure membrane 6, produced from silicone. The closure member 6 has a bell-shaped design and fits snugly on the inside against an inner shell of an upper half of the support housing 1, as can be seen from FIG. 1. In the region of the fluid passage, the elastically deformable closure member 6 is provided with a valve slit 7, which in the unloaded position according to FIG. 1 is closed in a sealed manner. As soon as a syringe or some other Luer connection part is placed onto the connection piece 3 and the Luer connecting portion 5, a corresponding connector portion of the syringe or of the Luer connection part presses an upper closure portion of the closure member 6 that surrounds the valve slit 7 inwards into the interior of the support housing 2, whereby the valve slit 7 is inevitably made to open elastically and opens a fluid passage between the syringe or the Luer connection part and the interior of the support housing 2.

Provided in the interior of the support housing 2 axially alongside the closure membrane 6 in the direction of the fluid is an orifice plate 10, which conducts a corresponding stream of fluid in the interior of the support housing 2. Also arranged in the support housing 2, on the side facing the opening 4, is a nonreturn valve 8, which is designed in the manner of a cone and has a swept cross-sectional shape that is made to extend in the form of a V towards the opening 4. The nonreturn valve 8 is formed by an elastomer element, which is restrained at its peripheral edge in the support housing 2. The nonreturn valve 8 is provided centrally with an elastically openable valve passage, which may be designed in the form of a slit. The nonreturn valve 8 is flanked on its side facing the fluid passage in the connection piece 3 by mechanical supporting means 9, which are configured as supporting webs that are made to extend parallel to the swept cross-sectional shape of the nonreturn valve 8 and are provided with apertures or as a differently designed, plate-like supporting structure. The supporting structure serving as mechanical supporting means 9 is fixedly connected to the support housing 2. The support housing 2 is of a two-part configuration, a lower half being provided with the opening 4 and an upper half being provided with the connection piece 3. The supporting structure 9 is of a one-part design with the orifice plate 10 and is fixed between the upper half and the lower half of the support housing 2 by adhesive bonding or by welding. Like the supporting structure 9 and the orifice plate 10, the support housing 2 consists of plastic.

The nonreturn valve 8 is capable of opening in both directions of the fluid, i.e. both in the direction of the connection piece 3 and in the direction of the opening 4. On account of the swept form, directed towards the opening 4, different pressure forces are necessary to open the nonreturn valve 8 in one direction or the other. In order to increase further the pressure forces that are necessary for opening the nonreturn valve 8 in the direction of the connection piece 3, the supporting structure 9 is assigned to the side of the nonreturn valve 8 that is facing the connection piece 3. The supporting structure 9 extends radially from the outside over most of the radial length of each side of the nonreturn valve 8 and stably supports the nonreturn valve 8 in the direction of the connection piece 3. For this purpose, the supporting structure has a much greater dimensional stability than the nonreturn valve 8. In the region of the slit passage, on the other hand, the nonreturn valve 8 is not supported by the supporting structure 9, and so in this region the nonreturn valve 8 can open towards the connection piece 3. Relatively high pressure forces are necessary for this, and so opening of the nonreturn valve 8 only takes place at a difference in pressure of the fluid between the side facing the opening 4 and the side facing the connection piece 3 of the nonreturn valve 8 that preferably lies above 10 hPa. In the opposite direction of the fluid, smaller differences in pressure between the two sides of the nonreturn valve 8 are already sufficient to open the nonreturn valve 8 towards the opening 4. The difference in opening pressure for the closure device 1 in the direction of the opening 4 is preferably around 2 hPa.

As soon as a corresponding syringe or some other Luer connection part is placed onto the connection piece 3 and the lower connecting portion 5, the slit 7 of the closure membrane 6 is in the open state, and so fluid can be introduced into the support housing 2 or can be extracted from the support housing 1 by way of the syringe or the other Luer connection part. When fluid is introduced, the nonreturn valve 8 opens in the direction of the opening 4, and so the fluid introduced can flow into the corresponding fluid reservoir or into the fluid line. If fluid is to be extracted from the fluid line or the fluid reservoir through the fluid passage of the connection piece 3, the syringe is filled or negative pressure is created in the Luer connection piece in some other way. As soon as this negative pressure is great enough, the nonreturn valve 9 opens towards the connection piece 3, and so the fluid can flow from the fluid reservoir or the fluid line by way of the opening 4 through the nonreturn valve 8 and also through the orifice plate 10 through the opened closure membrane 6 into the syringe or the other Luer connection part.

As a result of the support by means of the supporting structure 6 and as a result of the swept design of the nonreturn valve 8, the nonreturn valve 8 remains closed as long as there is only a negative pressure in the upper half of the support housing 1 that is produced by the removal of the syringe or the Luer connection part from the Luer connecting portion 5 and from the connection piece 3.

The closure device 1a according to FIGS. 2 and 3 has a similar construction to the closure device 1 that is shown in FIG. 1. Therefore, only the differences from this closure device 1 are discussed below. Portions or parts of the closure device 1a that are functionally the same are provided with the same designations, with the addition of the letter a. In the case of the closure device 1a that is shown in FIGS. 2 and 3, a nonreturn valve 8a is likewise provided in the support housing 2a, arranged between an orifice plate 10a and the opening 4a to a corresponding fluid reservoir or corresponding fluid line. The nonreturn valve 8a is in the same way designed in a swept manner conically in the direction of the opening 4a, as is the case with the nonreturn valve 8 according to FIG. 1. The main difference from the embodiment that is shown in FIG. 1 is that the nonreturn valve 8a is not assigned a mechanical supporting structure. Rather, a pressure equalization is created in a fluid space within the support housing 2a that is bounded by the nonreturn valve 8a on the one hand and the closure member 6a on the other hand, by elastically flexible, thin-walled wall portions 11 of the closure membrane, which can curve inwards towards the middle of the support housing 2a. Pressure-equalizing openings 12 are provided in the support housing 2a at the height of these flexible wall portions 11, in order to allow the elastic inward curving of these wall portions 11.

As a result, negative pressures occurring in the region of the connection piece 3a that may occur as a result of detachment of a syringe or other Luer connection part from the connection piece 3a while the closure membrane 6a is still open do not act directly on the nonreturn valve 8a, but instead are equalized by elastic inward curving of the wall portions 11. This has the effect that the nonreturn valve 8a remains in its closed position, and so an unintentional flow of fluid from the opening 4a through the nonreturn valve 8a can be reliably avoided.

Figure 5:
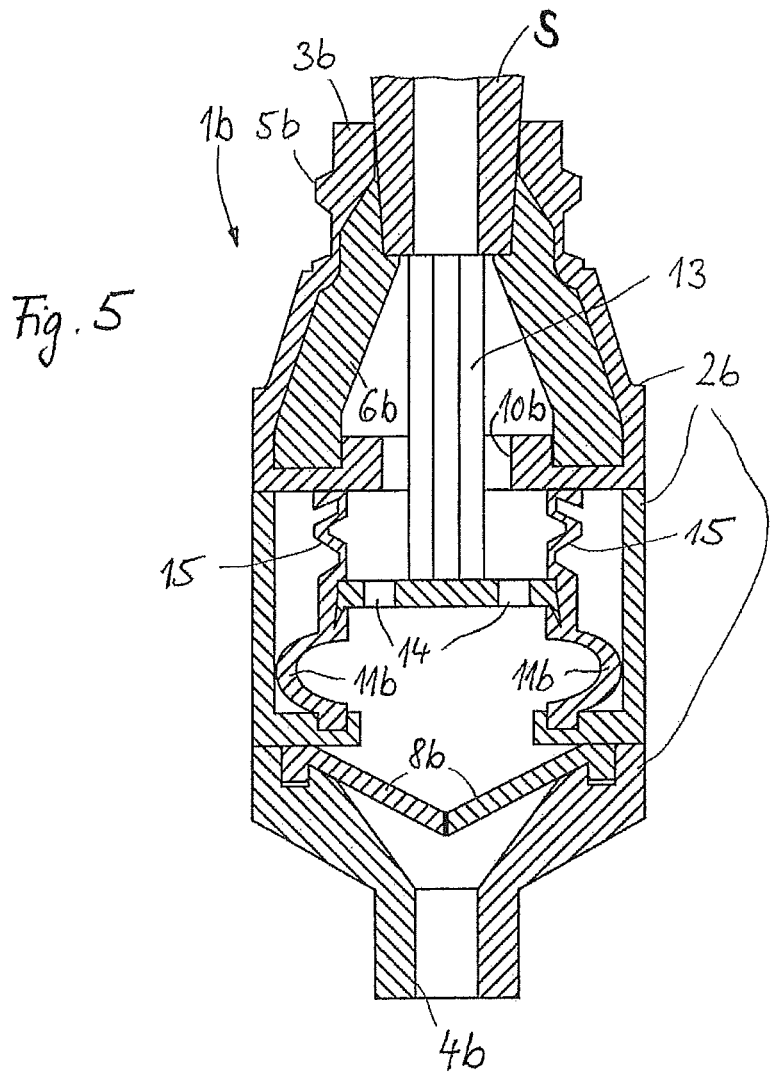

In the case of the embodiments that are shown in FIGS. 4 and 5, the closure device 1b likewise has parts and portions that are configured in functionally the same way as the closure device 1 and 1a described above. These parts and portions that are functionally the same are provided with the same designations, with the addition of the letter b. Also with respect to the closure device 1b that is shown in FIGS. 4 and 5, to avoid repetition only the differences from the previously described embodiments are discussed below. The closure device 1b has a support housing 2b, which is provided on one side with a connection piece 3b and on an opposite side with an opening 4b to a fluid reservoir or fluid line. The fluid passage in the region of the connection piece 3b is closed by a closure membrane 6b provided with a slit 7b as long as there is no syringe S (FIG. 5) or some other Luer connection part coupled to the connection piece 3b. In the lower part enclosing the opening 4b, the support housing 2b is provided with a nonreturn valve 8b, which by analogy with the previously described embodiments is designed in a conically swept manner.

Between the upper part of the support housing 2b that encloses the closure membrane 6b and the lower part of the support housing 2b that receives the nonreturn valve 8b, the support housing 2b has an intermediate part, in the interior of which a pressure-equalizing chamber is formed in the way described below. The pressure-equalizing chamber has annular, elastically flexible wall portions 11b and 15, which run coaxially in relation to the longitudinal extent of the support housing 2b and are kept radially at a distance from an inner wall of the intermediate part of the support housing 2b. The radial distance serves the purpose of allowing an outward curving of the elastically flexible wall portions 11b to the outside according to FIG. 5. Held between the wall portions 11b and 15 as an adjusting means is a plunger 13, which comprises a plunger base, aligned transversely in relation to the direction of fluid flow within the pressure-equalizing chamber, and also a plunger column, which is taken up to the closure portion of the closure membrane 6b that surrounds the slit 7b and which has the cross section of a cross. The plunger column is taken through the orifice plate 10b and is supported on the inside against the closure portion of the closure membrane 6b that closes the fluid passage of the connection piece 3b. The plunger base is provided with multiple eccentrically arranged through-flow openings 14, in order to allow a fluid flow through the plunger base. The elastically flexible wall portions 11b and 15 are formed by an elastomer material. The wall portions 15 facing the orifice plate 10b are foldable in a fanfold manner. The annular wall portions 11b running between the nonreturn valve 8b and the plunger base can curve inwards or outwards in an elastically flexible manner. The pressure-equalizing chamber thus formed ensures that the nonreturn valve 8b only opens in the direction of the connection piece 3b at relatively great differences in pressure.

As soon as a syringe S is attached to the connection piece 3b by way of a corresponding Luer closure, a connector tip of the syringe S axially enters the connection piece 3b and opens the slit 7b of the closure membrane 6b by elastic deformation. At the same time, the plunger column of the plunger 13 is inevitably pressed axially inwards into the support housing, whereby the plunger base connected to the wall portions 11b and 15 is correspondingly displaced axially towards the opening 4b and the wall portions 15 and 11b are inevitably elastically deformed. The cross-like cross-sectional shape of the plunger 13 allows fluid to flow along the plunger column in both directions of the fluid and also to pass through the through-openings 14 in the plunger base in both directions of the fluid.

The embodiments according to FIGS. 2 to 5 are also designed in such a way that opening of the respective nonreturn valve 8a, 8b in the direction of the opening 4a, 4b, and consequently in the direction of the fluid reservoir or the fluid line, takes place at a difference in pressure of approximately 20 hPa, whereas opening of the nonreturn valve 8a, 8b in the opposite direction towards the connection piece 3a, 3b only takes place at a substantially greater difference in pressure of at least 100 hPa. The function of the pressure-equalizing chamber according to FIGS. 4 and 5 corresponds substantially to the function of the pressure-equalizing chamber according to FIGS. 2 and 3, with the difference that the elastic outward or inward curving of the corresponding wall portions 11b, 15 can take place within the closed support housing 2b, and accordingly there does not have to be an opening to the surroundings.

The invention claimed is:

1. A closure device for a fluid system for medical purposes, the closure device comprising:
   a support housing including at least one opening to a fluid reservoir or a fluid line;
   a connection piece, wherein the connection piece comprises a Luer connecting portion for connecting to a syringe or some other Luer connection part, and wherein the connection piece further comprises an elastically deformable closure membrane which closes a fluid passage of the connection piece and opens the fluid passage when the syringe or the other Luer connection part is connected; and
   a nonreturn valve that is capable of opening both in a direction of the connection piece and in a direction of the at least one opening to the fluid reservoir or the fluid line and is arranged in the support housing at a distance from the closure membrane in the direction of the at least one opening to the fluid reservoir or the fluid line, the nonreturn valve having a swept cross-sectional shape that is conical in a direction of the at least one opening to the fluid reservoir or the fluid line, and wherein a mechanical support means is disposed so as to flank a side of the nonreturn valve that faces the connection piece,
   the mechanical support means extending parallel to the swept cross-sectional shape of the nonreturn valve, and
   the nonreturn valve comprising a first region comprising a slit passage and a second region extending radially outward of the first region.

2. The closure device according to claim 1, wherein the nonreturn valve is designed in such a way that it opens in the direction of the at least one opening to the fluid reservoir or the fluid line at a smaller difference in pressure than in the direction of the connection piece.

3. The closure device according to claim 2, wherein the difference in pressure at which the nonreturn valve opens towards the at least one opening to the fluid reservoir or the fluid line is at least three times smaller to five times smaller than in the direction of the connection piece.

4. The closure device according to claim 2, wherein the difference in pressure at which the nonreturn valve opens towards the fluid passage of the connection piece is greater than a difference in pressure that is created when the syringe or the other Luer connection part of the support housing is detached.

5. The closure device according to claim 1, wherein the mechanical support means flanking the nonreturn valve on the one side is provided in the support housing, in order only to bring about opening of the nonreturn valve in the direction of the connection piece at a greater difference in pressure than in the direction of the at least one opening to the fluid reservoir or the fluid line.

6. The closure device according to claim 1, wherein the support housing is of a one-part or multi-part configuration.

7. The closure device according to claim 1, wherein the nonreturn valve is supported by the mechanical support means in such a way that it opens in a direction of the connection piece at a difference in pressure of more than 10 hPa and in the direction of the at least one opening to the fluid reservoir or the fluid line at a difference in pressure of more than 2 hPa.

8. The closure device according to claim 1, wherein the mechanical support means comprises supporting webs.

9. The closure device according to claim 1, wherein the mechanical support means comprises apertures.

10. The closure device according to claim 1, wherein the mechanical support means extends over most of a radial length of the nonreturn valve.

11. The closure device according to claim 1, wherein the mechanical support means supports the second region of the nonreturn valve but not the first region.

* * * * *